US00PP19850P2

(12) United States Plant Patent
Delabroye

(10) Patent No.: US PP19,850 P2
(45) Date of Patent: Mar. 24, 2009

(54) ***GERANIUM* PLANT NAMED 'SANDRINE'**

(50) Latin Name: *Geranium l.*
Varietal Denomination: Sandrine

(75) Inventor: Thierry Delabroye, Hantay (FR)

(73) Assignee: Denis-Plants BVBA, Beervelde (BE)

( * ) Notice: Subject to any disclaimer, the term of this patent is extended or adjusted under 35 U.S.C. 154(b) by 0 days.

(21) Appl. No.: 12/012,934

(22) Filed: Feb. 6, 2008

Related U.S. Application Data

(60) Provisional application No. 60/925,743, filed on Apr. 23, 2007.

(51) Int. Cl.
*A01H 5/00* (2006.01)

(52) U.S. Cl. ..... Plt./324

(58) Field of Classification Search ..... Plt./324
See application file for complete search history.

*Primary Examiner*—Annette H Para
*Assistant Examiner*—S. B. McCormick-Ewoldt

(57) ABSTRACT

A new and distinct cultivar of *Geranium* plant named 'Sandrine' that is characterized by yellow immature leaves that change to yellow-green and then to green when mature, a creeping habit and purple flowers with a black center.

1 Drawing Sheet

Botanical classification: *Geranium* l.
Variety denomination: 'Sandrine'.

BACKGROUND OF THE INVENTION

The present invention relates to a new and distinct cultivar of *Geranium* plant botanically known as *Geranium* l. and hereinafter referred to by the cultivar name 'Sandrine'.

The new cultivar is the product of a breeding program conducted by the inventor in a cultivated area of Hantay, France.

'Sandrine' is a hybrid that originated from the hybridization of the female or seed parent *Geranium* 'Ann Folkard' (not patented) and the male or pollen parent *Geranium* 'Patricia' (not patented). The cultivar 'Sandrine' was selected by the inventor in the Spring of 2005 as a single plant within the progeny of the stated cross in a controlled environment of Hantay, France.

Asexual reproduction by tissue culture the new cultivar 'Sandrine' was first done in the Summer of 2005 in Hantay, France. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'Sandrine'. These traits in combination distinguish 'Sandrine' as a new and distinct cultivar apart from other known existing varieties of *Geranium.*

1. *Geranium* 'Sandrine' exhibits yellow immature leaves that change to yellow-green and then to green when mature.
2. *Geranium* 'Sandrine' exhibits a creeping habit.
3. *Geranium* 'Sandrine' exhibits purple flowers with a black center.

The closest comparison varieties are the parent plants. The new cultivar 'Sandrine' is distinguishable from the female parent *Geranium* 'Ann Folkard' in having larger flowers.

The new cultivar 'Sandrine' is distinguishable from the male parent *Geranium* 'Patricia' in having yellow immature leaves and a creeping habit. The immature leaves of 'Patricia' are green.

BRIEF DESCRIPTION OF THE DRAWING

The accompanying photograph illustrates the distinguishing traits of *Geranium* 'Sandrine'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'Sandrine'. Data was collected in Beervelde, Belgium from 12 week old plants grown under glass greenhouse conditions. The plants were grown in 9 cm diameter containers. The time of year was Winter and the average daytime temperature was 12° Centigrade. and the average night temperature was 4° Centigrade. Color determinations are in accordance with The Royal Horticultural Society Colour Chart 2001 edition, except where general color terms of ordinary dictionary significance are used. The growing requirements are similar to the species.

'Sandrine' has not been tested under all possible conditions and phenotypic differences may be observed with variations in environmental, climatic, and cultural conditions, however, without any variance in genotype.

Botanical classification: *Geranium* l. 'Sandrine'.
Parentage: 'Sandrine' resulted from the hybridization of the following plants:
*Female parent.*—*Geranium* 'Ann Folkard'.
*Male parent.*—*Geranium* 'Patricia'.
Vigor: Moderate.
Growth rate: Approximately 12 cm. per month.
Growth habit: Broad spreading.
Plant shape: Prostrate.

Plant height: Average 18 cm. in height.
Plant width: Average 37.5 cm. in width.
Suitable container size: 9 cm. containers.
Propagation: Tissue culture.
Time to initiate roots: Approximately 5–20 days to produce roots on an initial cutting.
Time to produce a rooted cutting or liner: Approximately 12–27 days.
Crop time: From a rooted cutting, approximately 20 weeks are required to produce a finished plant.
High temperature tolerance: 35° Centigrade.
Low temperature tolerance: USDA Zone 5.
Root system: Fine and fibrous.
Stem:
*Branching habit.*—Free branching.
*Basal branching.*—Yes.
*Average number of lateral branches.*—3.
*Pinching.*—No.
*Lateral branch dimensions.*—36.1 cm. in length and 3.5 cm. in diameter.
*Lateral branch strength.*—Moderate.
*Color.*—183B.
*Internode length.*—13.9 cm. between nodes.
*Shape.*—Round.
*Pubescence.*—Dense, soft, 0.75 mm. in length, color N155A.
Foliage:
*Texture.*—Dull and pubescent.
*Leaf arrangement.*—Rosette.
*Compound or single.*—Single.
*Quantity of leaves per lateral branch.*—7.
*Leaf shape.*—Orbicular to reniform.
*Leaf apex.*—Broad acute.
*Leaf base.*—Hastate.
*Leaf length.*—6.7 cm. in length.
*Leaf width.*—7.8 cm. in width.
*Pubescence.*—Both sides have short hairs, 0.75 mm in length and colored 155D; on under side hairs mainly on main and secondary veins, on upper side hairs mainly present on entire leaf blade.
*Leaf margin.*—Palmately parted, lobes biserrate.
*Vein pattern.*—Palmate.
*Young leaf color* (*upper surface*).—In between 143A and 144A.
*Young leaf color* (*lower surface*).—144A.
*Mature leaf color* (*upper surface*).—143A.
*Mature leaf color* (*lower surface*).—144A to 144B.
*Vein color* (*upper surface*).—144A to 144B.
*Vein color* (*lower surface*).—144B.
*Leaf attachment.*—Petiolate.
*Petiole dimensions.*—21.3 cm. in length and 1.5 mm. in width.
*Petiole color.*—146B, base 178B.
Stipules:
*Stipule shape.*—Ovate.
*Stipule tip.*—Acute.
*Stipule base.*—Cuneate.
*Stipule dimensions.*—8 mm. in length and 3 mm. in width.
*Stipule color.*—181C with a base 145A to 145B on both sides.
Inflorescence:
*Inflorescence arrangement.*—Paired.
*Inflorescence type.*—Single.
*Flowering habit.*—Continuous.
*Quantity of flowers per inflorescence.*—Average 2.
*Quantity of buds per lateral stem.*—Average 8.
*Quantity of flowers and buds per plant.*—Average 30.
*Flowering season.*—Spring to Fall.
*Time to flower.*—Approximately 6 months.
*Rate of flower opening.*—Approximately 5 of the flowers are opened at once.
*Fragrance.*—None.
*Bud dimensions.*—8 mm. in length and 4.5 mm. in diameter.
*Bud shape.*—Elliptic.
*Bud color.*—138A flushed with 183A to 183B.
*Rate of bud opening.*—4 days.
*Flower aspect.*—Upright to outward.
*Flower shape.*—Rotate, single.
*Flower dimensions.*—4.4 cm. in diameter and 1.4 cm. in height.
*Flower longevity.*—Lasts approximately 7 days on plant.
*Self-cleaning or persistent.*—Persistent.
*Petal texture.*—Glabrous.
*Pubescence.*—Toward petal base, 0.5 mm in length, color N155A.
*Petal arrangement.*—Rotate.
*Number of petals.*—5 in number.
*Petals fused or unfused.*—Unfused.
*Petal shape.*—Obcordate.
*Petal margin.*—Entire.
*Petal apex.*—Obtuse.
*Petal dimensions.*—2.1 cm. in length and 1.9 cm. in width.
*Petal color when opening* (*upper side*).—N78A with base and veins N186A to 202A.
*Petal color when opening* (*under side*).—N74A to N78A with base and veins N186A to 202A.
*Petal color fully opened* (*upper side*).—N78A with base and veins N186A to 202A.
*Petal color fully opened* (*under side*).—N74A to N78A with base and veins N186A to 202A.
Sepals:
*Number of sepals.*—5.
*Sepal arrangement.*—Rotate.
*Sepal surface.*—Dull, Lower side: pubescent.
*Sepal shape.*—Elliptic.
*Sepal margin.*—Entire.
*Sepal apex.*—Mucronate.
*Sepal base.*—Cuneate.
*Sepal dimensions.*—1.2 cm. in length and 4 mm. in width.
*Sepal color immature* (*upper side*).—144A.
*Sepal color immature* (*under side*).—138A to 138B.
*Sepal color mature* (*upper side*).—146B.
*Sepal color mature* (*under side*).—148A.
*Calyx shape.*—Rotate, slightly cupped.
*Calyx dimensions.*—6 mm. in length, 2.7 cm. in diameter.
Peduncle:
*Peduncle dimensions.*—8 cm. in length and 1.2 mm. in diameter.
*Peduncle angle.*—35° from vertical.
*Peduncle color.*—144A to 144B, one side 176B.
*Peduncle strength.*—Moderately strong.
Pedicels:
*Pedicel dimensions.*—4.5 cm. in length and 1.0 mm. in diameter.
*Pedicel angle.*—25° from vertical.
*Pedicel color.*—144B, one side flushed with 176B.

*Pedicel strength.*—Moderate.

Reproduction organs:

*Stamen number.*—10.

*Anther shape.*—Dorsifixed, Oblong.

*Anther dimensions.*—2.5 mm. in length, 1 mm. in width.

*Anther color.*—N186A to 202A.

*Amount of pollen.*—Moderate.

*Pollen color.*—12A.

*Pistil number.*—1 in number.

*Pistil dimensions.*—5 mm. in length.

*Stigma shape.*—Five parted, decurrent.

*Stigma color.*—N186C.

*Style length.*—3.5 mm

*Style color.*—46A.

*Ovary color.*—138B.

*Ovary pubescence.*—Dense, 0.3 mm. in length, color N155A.

Seed: Seed production has not been observed.

Disease and pest resistance: Plants of the new *geranium* have not been observed for disease or pest resistance.

What is claimed is:

1. A new and distinct variety of *Geranium* plant named 'Sandrine' as described and illustrated.

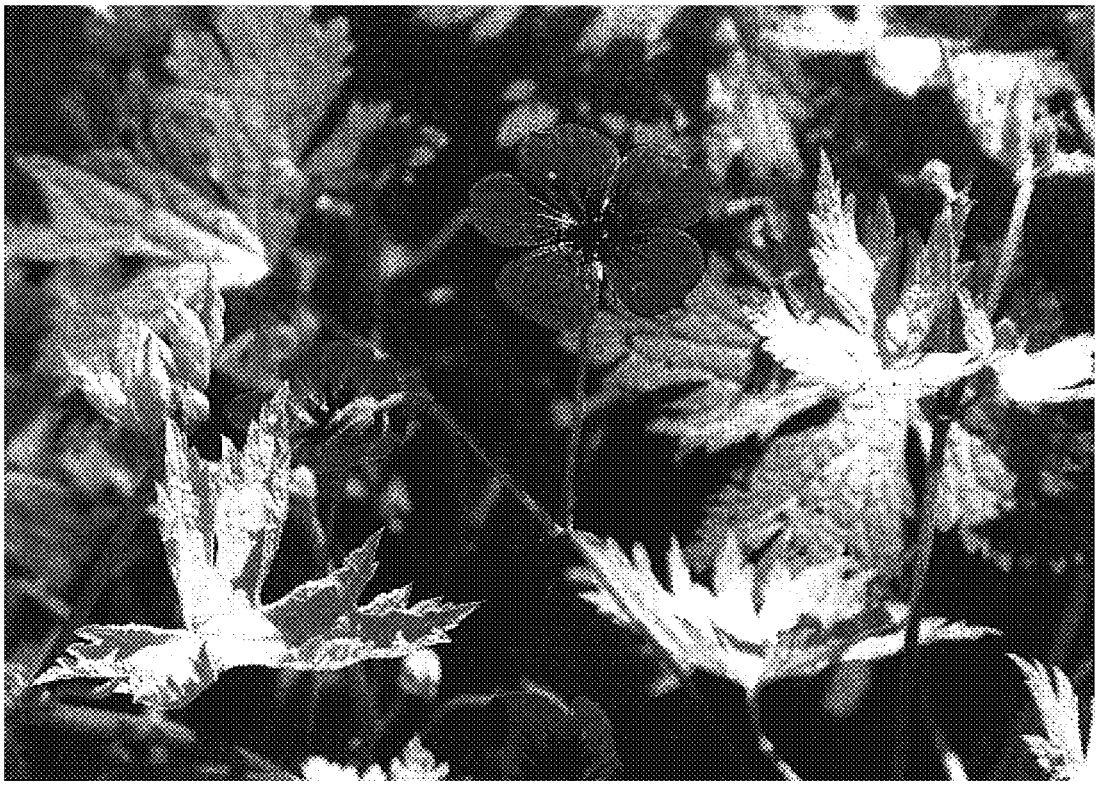

* * * * *